United States Patent
Sato

(10) Patent No.: US 11,944,496 B2
(45) Date of Patent: Apr. 2, 2024

(54) ULTRASOUND ENDOSCOPE

(71) Applicant: OLYMPUS CORPORATION, Tokyo (JP)

(72) Inventor: Sunao Sato, Yamato (JP)

(73) Assignee: OLYMPUS CORPORATION, Tokyo (JP)

( * ) Notice: Subject to any disclaimer, the term of this patent is extended or adjusted under 35 U.S.C. 154(b) by 214 days.

(21) Appl. No.: 17/735,513

(22) Filed: May 3, 2022

(65) Prior Publication Data

US 2022/0257215 A1    Aug. 18, 2022

Related U.S. Application Data

(63) Continuation of application No. PCT/JP2019/044202, filed on Nov. 11, 2019.

(51) Int. Cl.
*A61B 8/04* (2006.01)
*A61B 1/04* (2006.01)
(Continued)

(52) U.S. Cl.
CPC .............. *A61B 8/4494* (2013.01); *A61B 1/04* (2013.01); *A61B 8/12* (2013.01); *A61B 8/445* (2013.01);
(Continued)

(58) Field of Classification Search
CPC ........... A61B 8/4494; A61B 1/04; A61B 8/12; A61B 8/445; A61B 1/05; A61B 1/07;
(Continued)

(56) References Cited

U.S. PATENT DOCUMENTS 5,222,483 A * 6/1993 Plisek ...................... G10K 9/12
601/4
5,669,389 A * 9/1997 Rotteveel ................. A61B 8/12
600/459

(Continued)

FOREIGN PATENT DOCUMENTS

JP       2006-204642 A    8/2006
JP          4488203 B2    6/2010

OTHER PUBLICATIONS

International Search Report dated Jan. 28, 2020 received in PCT/JP2019/044202.

*Primary Examiner* — Angela M Hoffa
*Assistant Examiner* — Adil Partap S Virk
(74) *Attorney, Agent, or Firm* — Scully, Scott, Murphy & Presser, P.C.

(57) ABSTRACT

An ultrasound endoscope includes: a plurality of piezoelectric elements that are arranged to form a cylinder such that respective longitudinal directions of the piezoelectric elements are aligned, each piezoelectric element being configured to transmit and receive an ultrasound wave; an acoustic lens that is located on outer peripheries of the piezoelectric elements, the acoustic lens being configured to converge ultrasound waves generated by the piezoelectric elements on an outside of the acoustic lens, and transmit ultrasound waves input from the outside of the acoustic lens to the piezoelectric elements; a housing configured to hold distal end sides and proximal end sides of both of the piezoelectric elements and the acoustic lens; and a flexible material that is located between either a distal end or a proximal end of the acoustic lens and the housing, and that has a lower elastic modulus than the acoustic lens.

9 Claims, 3 Drawing Sheets

(51) Int. Cl.
  *A61B 8/00* (2006.01)
  *A61B 8/12* (2006.01)
  *B06B 1/06* (2006.01)

(52) U.S. Cl.
  CPC ........ *B06B 1/0633* (2013.01); *B06B 2201/76* (2013.01)

(58) Field of Classification Search
  CPC ... A61B 8/4483; A61B 8/4488; B06B 1/0633; B06B 2201/76
  See application file for complete search history.

(56) References Cited

U.S. PATENT DOCUMENTS

| | | | |
|---|---|---|---|
| 5,685,823 A * | 11/1997 | Ito | A61B 1/05 600/156 |
| 6,142,930 A * | 11/2000 | Ito | A61B 1/00096 600/110 |
| 2005/0070801 A1 * | 3/2005 | Yamashita | A61B 8/4281 600/459 |
| 2006/0009681 A1 | 1/2006 | Tanaka et al. | |
| 2006/0025691 A1 | 2/2006 | Tanaka et al. | |
| 2007/0287920 A1 * | 12/2007 | Sawada | B06B 1/067 600/463 |
| 2008/0119738 A1 * | 5/2008 | Imahashi | A61B 1/00114 600/182 |
| 2009/0275839 A1 | 11/2009 | Sawada et al. | |
| 2010/0049054 A1 | 2/2010 | Sawada et al. | |
| 2011/0218443 A1 | 9/2011 | Sawada et al. | |
| 2017/0196538 A1 * | 7/2017 | Sato | A61B 8/4483 |
| 2022/0395256 A1 * | 12/2022 | Løype | A61B 8/14 |

\* cited by examiner

ULTRASOUND ENDOSCOPE

CROSS-REFERENCE TO RELATED APPLICATION

This application is a continuation of International Application No. PCT/JP2019/044202, filed on Nov. 11, 2019, the entire contents of which are incorporated herein by reference.

BACKGROUND

1. Technical Field

The present disclosure relates to an ultrasound endoscope.

2. Related Art

In the related art, an ultrasound endoscope of a radial type, in which piezoelectric elements are arranged in a cylinder manner, has been used (for example, see Japanese Patent No. 4488203). Ultrasound waves emitted from the piezoelectric elements are applied to an inside of a subject through an acoustic lens that is located on outer peripheries of the piezoelectric elements. The acoustic lens is made of a flexible material, such as silicone, and the piezoelectric elements and the acoustic lens are held by a housing.

SUMMARY

In some embodiments, an ultrasound endoscope includes: a plurality of piezoelectric elements that are arranged to form a cylinder such that respective longitudinal directions of the piezoelectric elements are aligned, each piezoelectric element being configured to transmit and receive an ultrasound wave; an acoustic lens that is located on outer peripheries of the piezoelectric elements, the acoustic lens being configured to converge ultrasound waves generated by the piezoelectric elements on an outside of the acoustic lens, and transmit ultrasound waves input from the outside of the acoustic lens to the piezoelectric elements; a housing configured to hold distal end sides and proximal end sides of both of the piezoelectric elements and the acoustic lens; and a flexible material that is located between either a distal end or a proximal end of the acoustic lens and the housing, and that has a lower elastic modulus than the acoustic lens.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound endoscope according to the disclosure will be described below with reference to the drawings. The disclosure is not limited by the embodiments below. The disclosure is applicable to a general ultrasound endoscope including an ultrasound transducer of a radial type.

Further, in descriptions of the drawings, the same or corresponding components are appropriately denoted by the same reference symbols. Furthermore, it is necessary to note that the drawings are schematic, and dimensional relations of each of components, ratios among components, and the like may be different from actual ones. Moreover, the drawings may include a portion that has different dimensional relations or ratios.

Embodiment

Figure 1:
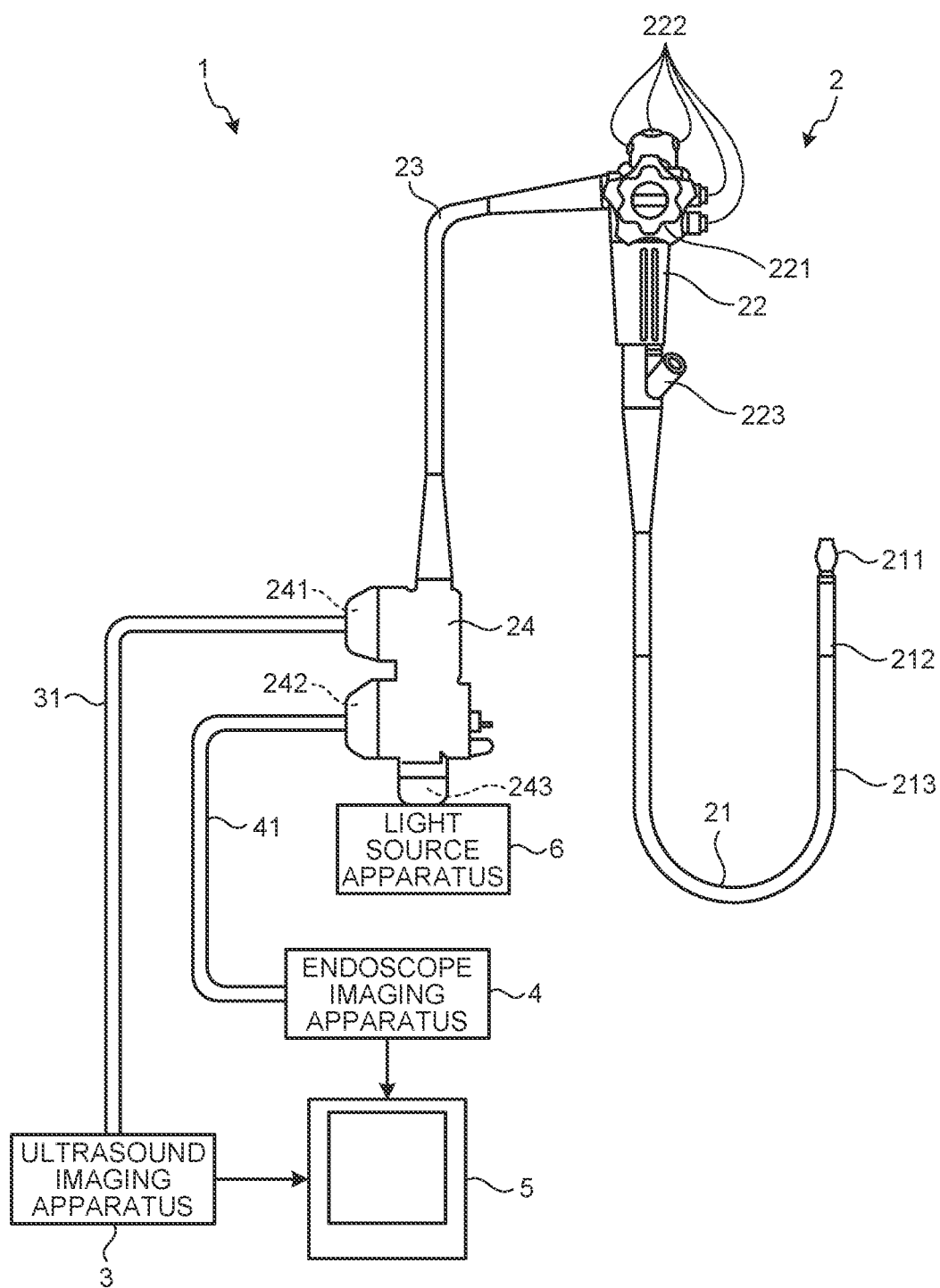
FIG. 1 is a diagram schematically illustrating an ultrasound endoscope system including an ultrasound endoscope according to one embodiment.

Overall Configuration of Ultrasound Endoscope System
FIG. 1 is a diagram schematically illustrating an ultrasound endoscope system including an ultrasound endoscope according to one embodiment. An ultrasound endoscope system 1 according to one embodiment is a system that performs an ultrasound diagnosis on a subject, such as a human being, by using an ultrasound endoscope. As illustrated in FIG. 1, the ultrasound endoscope system 1 includes an ultrasound endoscope 2, an ultrasound imaging apparatus 3, an endoscope imaging apparatus 4, a display apparatus 5, and a light source apparatus 6.

The ultrasound endoscope 2 is a combination of an endoscope imaging unit, which includes an observation optical system configured with a lens or the like and which includes an image sensor, with an ultrasound probe, and has an endoscope imaging function (endoscope observation function) and an ultrasound imaging function (ultrasound observation function). The ultrasound endoscope 2 is an ultrasound endoscope of a radial type that performs ultrasound observation in a direction perpendicular to a direction in which an insertion portion is inserted.

The ultrasound endoscope 2 includes, at a distal end thereof, an ultrasound transducer that converts an electric pulse signal transmitted from the ultrasound imaging apparatus 3 into an ultrasound pulse (acoustic pulse), applies the ultrasound pulse to the subject, converts an ultrasound echo reflected by the subject into an electrical echo signal that represents the ultrasound echo by a voltage change, and outputs the electrical echo signal. A configuration of the ultrasound transducer will be described later.

The ultrasound endoscope 2 includes an illuminator that applies illumination light to the subject, and an imager that receives reflected light from the subject. The illuminator includes a light guide that guides the illumination light to be applied to the subject to the distal end of the ultrasound endoscope 2 at the time of optical imaging. A distal end of the light guide reaches a distal end of the insertion portion of the ultrasound endoscope 2 inserted into the subject, and a proximal end portion is connected to the light source apparatus 6 that generates the illumination light. The imager includes an imaging optical system and an image sensor, is inserted into a digestive tract (an esophagus, a stomach, a duodenum, or a large intestine) or a respiratory organ (a trachea or a bronchus) of the subject, and is able to capture images of the digestive tract or the respiratory organ. Further, the ultrasound endoscope 2 is able to capture images of organs (a pancreas, a gallbladder, a bile duct, a pancreatic duct, lymph nodes, an organ in a mediastinum, a blood vessel, and the like) around the digestive tract or the respiratory organ by using ultrasound waves.

The ultrasound imaging apparatus 3 is electrically connected to the ultrasound endoscope 2 via an ultrasound cable 31, outputs a pulse signal to the ultrasound endoscope 2 via the ultrasound cable 31, and receives input of an echo signal from the ultrasound endoscope 2 via the ultrasound cable 31. Further, the ultrasound imaging apparatus 3 performs a predetermined process on the echo signal and generates an ultrasound image.

The endoscope imaging apparatus 4 is electrically connected to the ultrasound endoscope 2 via a video cable 41, and receives input of an image signal from the ultrasound endoscope 2 via the video cable 41. Further, the endoscope imaging apparatus 4 performs a predetermined process on the image signal and generates an endoscopic image.

The display apparatus 5 is configured with liquid crystal, organic electro luminescence (EL), or the like, and displays the ultrasound image generated by the ultrasound imaging apparatus 3, the endoscopic image generated by the endoscope imaging apparatus 4, and the like.

The light source apparatus 6 supplies the illumination light to the ultrasound endoscope 2 via the light guide.

Configuration of Ultrasound Endoscope

As illustrated in FIG. 1, the ultrasound endoscope 2 includes an insertion portion 21, an operating unit 22, a universal cord 23, and a connector 24. Meanwhile, the "distal end" described herein indicates an end portion located at a side of a distal end in a direction in which the insertion portion 21 is inserted into the subject. Further, the "proximal end" described herein indicates an end portion located at an opposite side (at a side of the operating unit 22) of the distal end in the direction in which the insertion portion 21 is inserted into the subject.

The insertion portion 21 is a tubular portion to be inserted into the subject. As illustrated in FIG. 1, the insertion portion 21 includes an ultrasound transducer 211 that is located at the distal end of the insertion portion 21, a bending portion 212 that is connected to a proximal end side of the ultrasound transducer 211 and that is bendable, and a flexible tube portion 213 that is connected to a proximal end side of the bending portion 212 and that has flexibility. A configuration of the distal end of the insertion portion 21 will be described later.

The ultrasound transducer 211 applies ultrasound waves in a direction perpendicular to a longitudinal direction of the insertion portion 21. The ultrasound transducer 211 includes a plurality of piezoelectric elements to be described later, and electronically performs scanning by electronically switching the piezoelectric elements related to transmission and reception or delaying transmission and reception performed by each of the piezoelectric elements. The ultrasound transducer 211 applies ultrasound waves to the inside of the subject due to vibration of the piezoelectric elements that occurs by input of a pulse signal. Further, if ultrasound waves reflected by the subject are transmitted to the piezoelectric elements, the piezoelectric elements vibrate due to the transmitted ultrasound waves, and the piezoelectric elements convert the vibration to an electrical signal (echo signal). The echo signal is transmitted to the ultrasound imaging apparatus 3 via the ultrasound cable 31 or the like.

The operating unit 22 is a portion that is connected to a proximal end side of the insertion portion 21 and receives various kinds of operation from a doctor or the like. As illustrated in FIG. 1, the operating unit 22 includes a bending knob 221 for performing bending operation on the bending portion 212, and a plurality of operating members 222 for performing various kinds of operation. Furthermore, a treatment tool insertion port 223 for inserting a treatment tool into a treatment tool insertion path is formed on the operating unit 22.

The universal cord 23 is a cable which extends from the operating unit 22 and in which a plurality of signal cables for transmitting various signals, an optical fiber for transmitting the illumination light supplied from the light source apparatus 6, and the like are arranged.

The connector 24 is arranged at a distal end of the universal cord 23. Further, the connector 24 includes first to third connectors 241 to 243 that are connected to the ultrasound cable 31, the video cable 41, and the light source apparatus 6, respectively.

Configuration of Distal End of Insertion Portion

Figure 2:
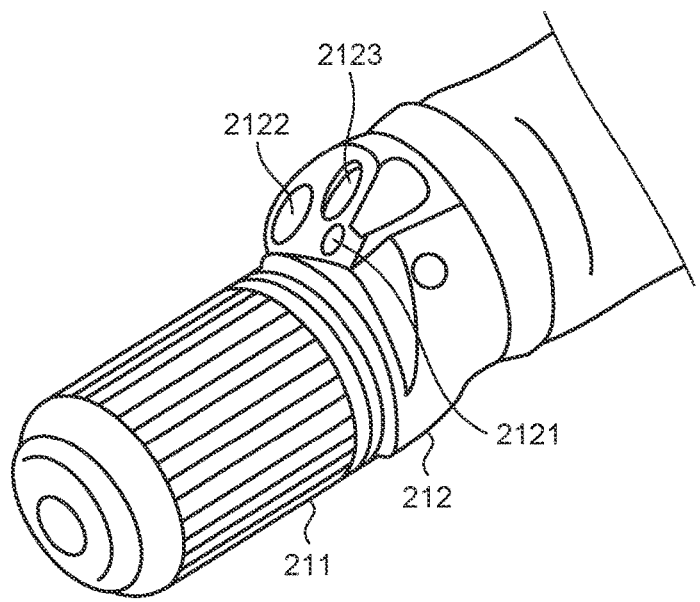
FIG. 2 is a perspective view of a distal end of an insertion portion of the ultrasound endoscope illustrated in FIG. 1.

FIG. 2 is a perspective view of the distal end of the insertion portion of the ultrasound endoscope illustrated in FIG. 1. As illustrated in FIG. 2, on the distal end of the insertion portion 21, an illuminator 2121 that applies the illumination light from the light source apparatus 6 to the subject, an imager 2122 including an image sensor that receives reflected light from the subject, a forceps port 2123 that also functions as a suction port, and an air transmission/water transmission nozzle (not illustrated) are arranged.

Figure 3:
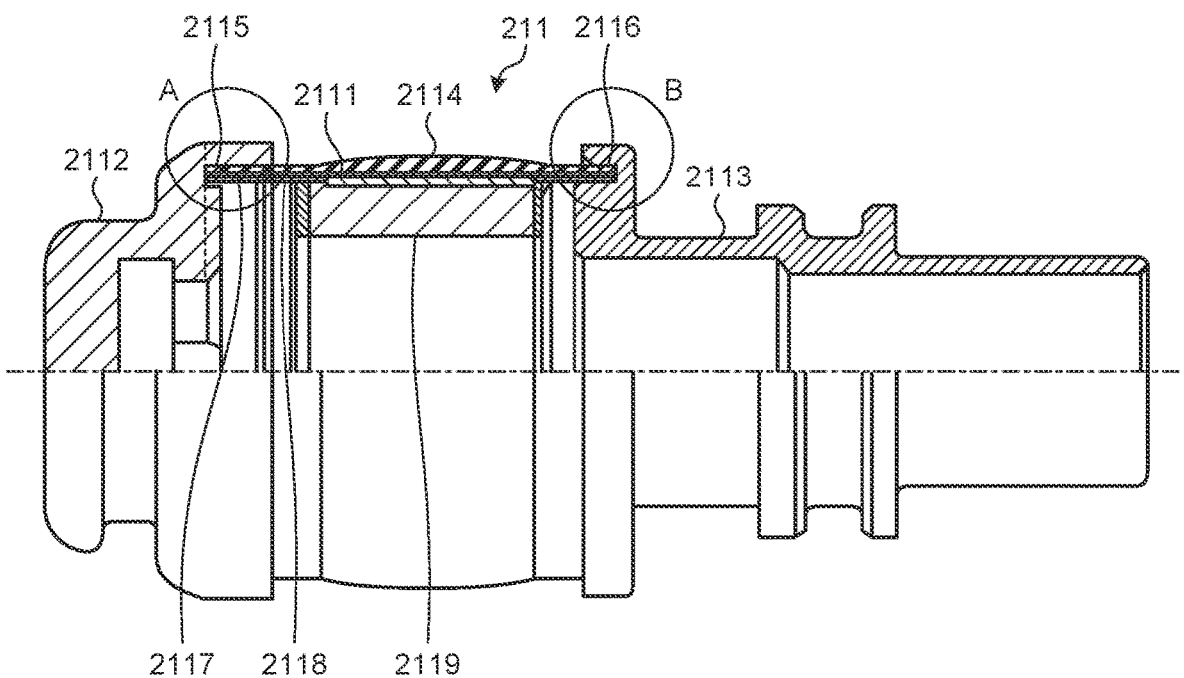
FIG. 3 is an enlarged cross-sectional view of the distal end of the insertion portion of the ultrasound endoscope illustrated in FIG. 1.

FIG. 3 is an enlarged cross-sectional view of the distal end of the insertion portion of the ultrasound endoscope illustrated in FIG. 1. As illustrated in FIG. 3, the ultrasound endoscope 2 includes piezoelectric elements 2111, a distal-end-side housing 2112, a proximal-end-side housing 2113, an acoustic lens 2114, a distal-end-side flexible material 2115, a proximal-end-side flexible material 2116, a first acoustic matching layer 2117, a second acoustic matching layer 2118, and a backing member 2119.

The plurality of piezoelectric elements 2111 have elongated shapes and arranged in a cylinder manner such that respective longitudinal directions (horizontal directions along the sheet of FIG. 3) are aligned. Each of the piezoelectric elements 2111 transmits and receives ultrasound waves. Specifically, each of the piezoelectric elements 2111 converts an electrical pulse signal into an acoustic pulse, applies the acoustic pulse to the subject, converts an ultrasound echo reflected by the subject into an electrical echo signal that represents the ultrasound echo by a voltage change, and outputs the electrical echo signal.

The distal-end-side housing 2112 holds distal end sides of the piezoelectric elements 2111 and the acoustic lens 2114. The distal-end-side housing 2112 is made of a hard material, such as a resin, a metal, or an alloy. The distal-end-side housing 2112 may be configured in an integrated manner with the proximal-end-side housing 2113, or may be configured as a separate body from the proximal-end-side housing 2113.

The proximal-end-side housing 2113 holds proximal end sides of the piezoelectric elements 2111 and the acoustic lens 2114.

The acoustic lens 2114 is located on outer peripheries of the piezoelectric elements 2111, converges the ultrasound waves generated by the piezoelectric elements 2111 on the outside, and transmits ultrasound waves emitted from the outside to the piezoelectric elements 2111. The acoustic lens 2114 is made of a flexible material, such as silicone, includes one surface that has a convex shape or a concave shape to implement a function to converge the ultrasound waves, outputs the ultrasound waves that have transmitted through the second acoustic matching layer 2118 to the outside, and receives ultrasound echoes from the outside.

Figure 4:
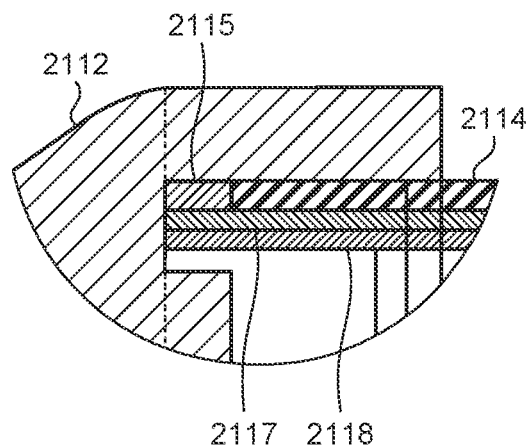
FIG. 4 is a partial enlarged view of a region A illustrated in FIG. 3.

FIG. 4 is a partial enlarged view of a region A illustrated in FIG. 3. As illustrated in FIG. 4, the distal-end-side flexible material 2115 is located between the distal end of the acoustic lens 2114 and the distal-end-side housing 2112, and has a lower elastic modulus than the acoustic lens 2114. Specifically, the distal-end-side flexible material 2115 is made of an elastic body, such as gel, or a flexible material, such as rubber.

Figure 5:
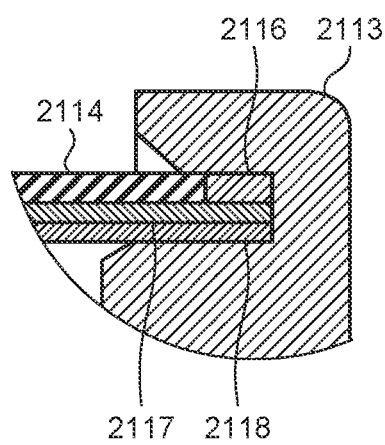
FIG. 5 is a partial enlarged view of a region B illustrated in FIG. 3.

FIG. 5 is a partial enlarged view of a region B illustrated in FIG. 3. As illustrated in FIG. 5, the proximal-end-side flexible material 2116 is located between the proximal end of the acoustic lens 2114 and the proximal-end-side housing 2113, and has a lower elastic modulus than the acoustic lens 2114. Specifically, the proximal-end-side flexible material 2116 is made of an elastic body, such as gel, or a flexible material, such as rubber.

The first acoustic matching layer 2117 and the second acoustic matching layer 2118 match acoustic impedance of the piezoelectric elements 2111 and acoustic impedance of the subject so as to effectively transmit ultrasound waves between the piezoelectric elements 2111 and the subject.

The backing member 2119 is made of a material with a large attenuation factor, such as epoxy resin in which filler, e.g., alumina or zirconia, is dispersed, or rubber in which the above-described filler is dispersed, and attenuates unnecessary ultrasound vibration that is generated by operation of the piezoelectric elements 2111.

As described above, according to one embodiment, the distal-end-side flexible material 2115 is arranged between the distal-end-side housing 2112 and the acoustic lens 2114, so that a stress that is applied from the distal-end-side housing 2112 to the acoustic lens 2114 is reduced. Similarly, the proximal-end-side flexible material 2116 is arranged between the proximal-end-side housing 2113 and the acoustic lens 2114, so that a stress that is applied from the proximal-end-side housing 2113 to the acoustic lens 2114 is reduced. As a result, it is possible to prevent deformation of the acoustic lens 2114 due to the stress, so that it is possible to prevent degradation in ultrasound performance of the ultrasound endoscope 2.

Meanwhile, in a radial direction of the piezoelectric elements 2111 arranged in a cylinder manner, it is preferable to set thicknesses of the distal-end-side flexible material 2115 and the proximal-end-side flexible material 2116 to be equal to or larger than a thickness of the acoustic lens 2114. If the thicknesses of the distal-end-side flexible material 2115 and the proximal-end-side flexible material 2116 are equal to or larger than the thickness of the acoustic lens 2114 in the radial direction, it is possible to improve an effect to reduce the stress that is applied from the distal-end-side housing 2112 or the proximal-end-side housing 2113 to the acoustic lens 2114. Meanwhile, the thickness of the acoustic lens 2114 is a thickness of each of end portions of the acoustic lens 2114 that come into contact with the distal-end-side flexible material 2115 and the proximal-end-side flexible material 2116.

Furthermore, in one embodiment as described above, the example has been described in which the flexible materials are located between the distal-end-side housing 2112 and the acoustic lens 2114 and between the proximal-end-side housing 2113 and the acoustic lens 2114, but it may be possible to arrange the flexible material between one of the distal end and the proximal end of the acoustic lens 2114 and the housing. In this case, the stress that is applied from the housing to the acoustic lens 2114 is reduced in a portion in which the flexible material is arranged.

According to one embodiment of the disclosure, in an ultrasound endoscope of a radial type, it is possible to implement an ultrasound endoscope capable of preventing degradation of ultrasound observation performance due to application of a stress to an acoustic lens.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope comprising:
a plurality of piezoelectric elements that are arranged to form a cylinder such that respective longitudinal directions of the piezoelectric elements are aligned, each piezoelectric element being configured to transmit and receive an ultrasound wave;
an acoustic lens that is located on outer peripheries of the piezoelectric elements, the acoustic lens being configured to converge ultrasound waves generated by the piezoelectric elements on an outside of the acoustic lens, and transmit ultrasound waves input from the outside of the acoustic lens to the piezoelectric elements;
a housing configured to hold distal end sides and proximal end sides of both of the piezoelectric elements and the acoustic lens; and
a flexible material that is located between either a distal end or a proximal end of the acoustic lens and the housing, and that has a lower elastic modulus than the acoustic lens; and
wherein the acoustic lens is made of silicone.

2. The ultrasound endoscope according to claim 1, wherein the flexible material is located between the distal end of the acoustic lens and the housing and between the proximal end of the acoustic lens and the housing.

3. The ultrasound endoscope according to claim 1, wherein in a radial direction of the cylinder, a thickness of the flexible material is equal to or larger than a thickness of the acoustic lens.

4. The ultrasound endoscope according to claim 1, further comprising:
an illuminator configured to apply illumination light to a subject; and
an imager that includes an image sensor configured to receive reflected light from the subject.

5. The ultrasound endoscope according to claim 1, wherein
the housing includes a recess for housing one of a distal end side and a proximal end side of the acoustic lens, and
the flexible material is arranged in the recess.

6. The ultrasound endoscope according to claim 5, wherein the flexible material is in contact with an inner surface of the recess and the acoustic lens.

7. The ultrasound endoscope according to claim 1, wherein the flexible material is made of one of gel and rubber.

8. The ultrasound endoscope according to claim 1, wherein the flexible material is configured to reduce a stress that is applied to the acoustic lens.

9. The ultrasound endoscope according to claim 7, wherein the flexible material is configured to reduce a stress in an axial direction including the proximal end of the acoustic lens and the distal end of the acoustic lens.

\* \* \* \* \*